US00PP26562P3

(12) United States Plant Patent
Suphachadiwong

(10) Patent No.: US PP26,562 P3
(45) Date of Patent: Mar. 29, 2016

(54) ***SANSEVIERIA* PLANT NAMED 'SUPSAN1301'**

(50) Latin Name: *Sansevieria aeethiopica×cylindrica*
Varietal Denomination: SUPSAN1301

(71) Applicant: Thumrong Suphachadiwong, Chonburi (TH)

(72) Inventor: Thumrong Suphachadiwong, Chonburi (TH)

(73) Assignee: Suphachatwong Innovation (TH)

( * ) Notice: Subject to any disclaimer, the term of this patent is extended or adjusted under 35 U.S.C. 154(b) by 120 days.

(21) Appl. No.: 14/120,141

(22) Filed: Apr. 28, 2014

(65) Prior Publication Data

US 2015/0313069 P1 Oct. 29, 2015

(51) Int. Cl.
*A01H 5/00* (2006.01)

(52) U.S. Cl.
USPC ..... Plt./382

(58) Field of Classification Search
USPC ..... Plt./382
See application file for complete search history.

*Primary Examiner* — Annette Para
(74) *Attorney, Agent, or Firm* — Cassandra Bright

(57) ABSTRACT

A new and distinct *Sansevieria* cultivar named 'SUPSAN1301' is disclosed, characterized by unique plant form, rosette leaf arrangement, and leaves that change from cylindrical to less terete as they mature. The new variety is a *Sansevieria,* typically produced as an indoor ornamental plant.

1 Drawing Sheet

Latin name of the genus and species: *Sansevieria aeethiopica×cylindrica.*
Variety denomination: 'SUPSAN1301'.

BACKGROUND OF THE INVENTION

This application relates to a new cultivar of *Sansevieria aeethiopica×cylindrica.* The new variety is the product of a planned breeding program, originating as a seedling from the open pollination of an unpatented, unnamed, proprietary seed parent *Sansevieria aeethiopica* with an unknown, unpatented, proprietary pollen parent variety of *Sanservieria cylindrica.* The actual pollen variety is unknown because the cross was made by means of open pollination process in a nursery where several proprietary hybrids of *Sanservieria cylindrica* were present. Any of the present hybrids could have acted as the pollen variety. All aforementioned *Sanservieria cylindrica* hybrids were created by the breeder and never commercially introduced or published and therefore do not have a variety name. The open pollination took place in 2003.

The new variety was first observed by the inventor, Thumrong Suphachadiwong, a citizen of Thailand, in 2005 after planting as a seedling in 2004 in a research greenhouse belonging to the inventor in Chonburi, Thailand. After identifying the new variety as a potentially interesting selection, the inventor continued confidential testing and propagation of 'SUPSAN1301', assessing stability of the unique characteristics of this variety.

Asexual reproduction of the new cultivar 'SUPSAN1301' was first performed at a research greenhouse belonging to the inventor in Chonburi, Thailand by leaf cuttings of original plant in 2005. Access to all plants was restricted, as plants were kept in a greenhouse not open to the public, belonging to the inventor, and not accessible to the public. Through subsequent propagation, more than 8 generations have been reproduced, which have shown that the unique features of this cultivar are stable and reproduced true to type.

SUMMARY OF THE INVENTION

The cultivar 'SUPSAN1301' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SUPSAN1301'. These characteristics in combination distinguish 'SUPSAN1301' as a new and distinct *Sansevieria* cultivar:

1. The young leaves of the candidate variety have a more cylindrical shape and as they mature, the form gradually changes from cylindrical to less and less terete.
2. Shape of plant; leaves arranged more as a rosette, rather than arranged in as a fan shape, or spiral which is common for *Sanservieria cylindrica* varieties.
3. Growth habit of the plant is unique as a whole.

PARENT COMPARISON

Plants of the new cultivar 'SUPSAN1301' are similar to the seed parent, the unpatented, unnamed, proprietary *Sansevieria aeethiopica* in most horticultural characteristics. However the new variety, 'SUPSAN1301' differs from seed parent in the following characteristics:

1. Leaves much longer and pointy, thicker in caliber and much more terete to cylindrical. Mother variety; leaves much flatter, shorter and broader.
2. More heavily branched, leaves arranged in a more rosette like way.
3. Taller less compact form.

Plants of the new cultivar 'SUPSAN1301' are similar to the possible but unknown pollen parent, *Sanservieria cylindrica* in most horticultural characteristics. However the new variety, 'SUPSAN1301' differs from possible pollen parent in the following characteristics:

1. Shorter leaves, less cylindrical than father variety. Leaves mature from more cylindrical to more terete.
2. Rosette growth form. Farther variety is of fan shape to spiraling form.
3. Leaf texture is smoother.

COMMERCIAL COMPARISON

There is no similar variety but 'SUPSAN1301' could perhaps be best compared with the unpatented commercial variety *Sanservieria cylindrica* 'Skyline' because the spotting of the leaf is somewhat similar. However the new variety, 'SUPSAN1301' differs from 'Skyline' in the following characteristics:

1. Leaves have slight arch. Comparator has straight leaves.
2. Branches very heavily. Branches produce many leaves with very short internodes. Comparator produces long branches which have leaves with very long internodes.
3. More rosette form. Comparator form is more fan shaped.
4. Very smooth leaf texture. Comparator leaf texture is coarse.
5. Leaves are less cylindrical to terete. Comparator leafs are more cylindrical.

BRIEF DESCRIPTION OF THE PHOTOGRAPH

The accompanying photograph in FIG. 1 illustrates in full color a typical plant of 'SUPSAN1301' grown in a commercial greenhouse in Honselersdijk, the Netherlands. The plant is 40 weeks old a 12 cm circular pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'SUPSAN1301' plant is bred in Chonburi, Thailand and hardened in a commercial greenhouse in Honselersdijk, the Netherlands. The plant is 35 weeks old in a 12 cm circular pot. Temperatures ranged between 22° C. to 40° C. during the day and 17° C. to 30° C. at night. No chemical treatments were given to the plants. Measurements and numerical values represent averages of typical plant types.

Botanical classification: *Sansevieria aeethiopica×cylindrical* 'SUPSAN1301'.

PROPAGATION

Time to initiate rooting: About 2 to 3 months at approximately 17° C. to 40 ° C.

Root description: Moderately thick, slightly fleshy, slightly fibrous, moderately dense, moderately branched, colored greyed-orange, near RHS N170B.

PLANT

Growth habit: Monopodial, rosulate.

Growth rate: Approximately 5 cm per month.

Height: Approximately 48.5 cm.

Plant spread: Approximately 36.5 cm.

Growth rate: Moderate. Approximately 5 cm per month.

Number of Leaves per plant of the above age: Average: 19.

FOLIAGE

Leaf:

*Arrangement.*—Rosulate.

*Average length.*—Approximately 34.5 cm (excl. sheath).

*Average width.*—Approximately 1.9 cm.

*Depth (thickness) of Leaf blade.*—Approximately 1.0 cm.

*Shape of blade.*—Linear, strongly carinate and succulent.

*Aspect.*—Leaves grow in an average angle of 65° to soil level (=0°=horizontal).

*Apex.*—Pungent, sharp to the touch.

*Base.*—Decurrent.

*Margin.*—Entire.

*Texture of surface.*—Glabrous, moderately glossy.

*Texture of bottom surface.*—Glabrous, moderately glossy.

Color:

*Young foliage upper side.*—Green; near RHS 143A, tip darker; near RHS 137A.

*Young foliage under side.*—Green; near RHS 137A.

*Mature foliage upper side.*—Green; in between near RHS N137A and 139A.

*Mature foliage under side.*—Green; near RHS N137D.

Venation:

*Type.*—Parallel.

*Color.*—Upper side: No veins visible on upper side. Under side: No veins visible on under side.

Sheath:

*Average length.*—Approximately 2.5 cm.

*Average width.*—Approximately 1.7 cm.

*Color.*—Yellow-green; near RHS 145C to 145D.

*Texture.*—Glabrous, moderately glossy.

Other distinguishing characteristics: No.

OTHER CHARACTERISTICS

Disease resistance: Neither resistance nor susceptibility to the normal diseases found in *Sansevieria* has been observed.

Fruit/seed production: No fruits/seeds detected to date.

What is claimed is:

1. A new and distinct cultivar of *Sansevieria* plant named 'SUPSAN1301' as herein illustrated and described.

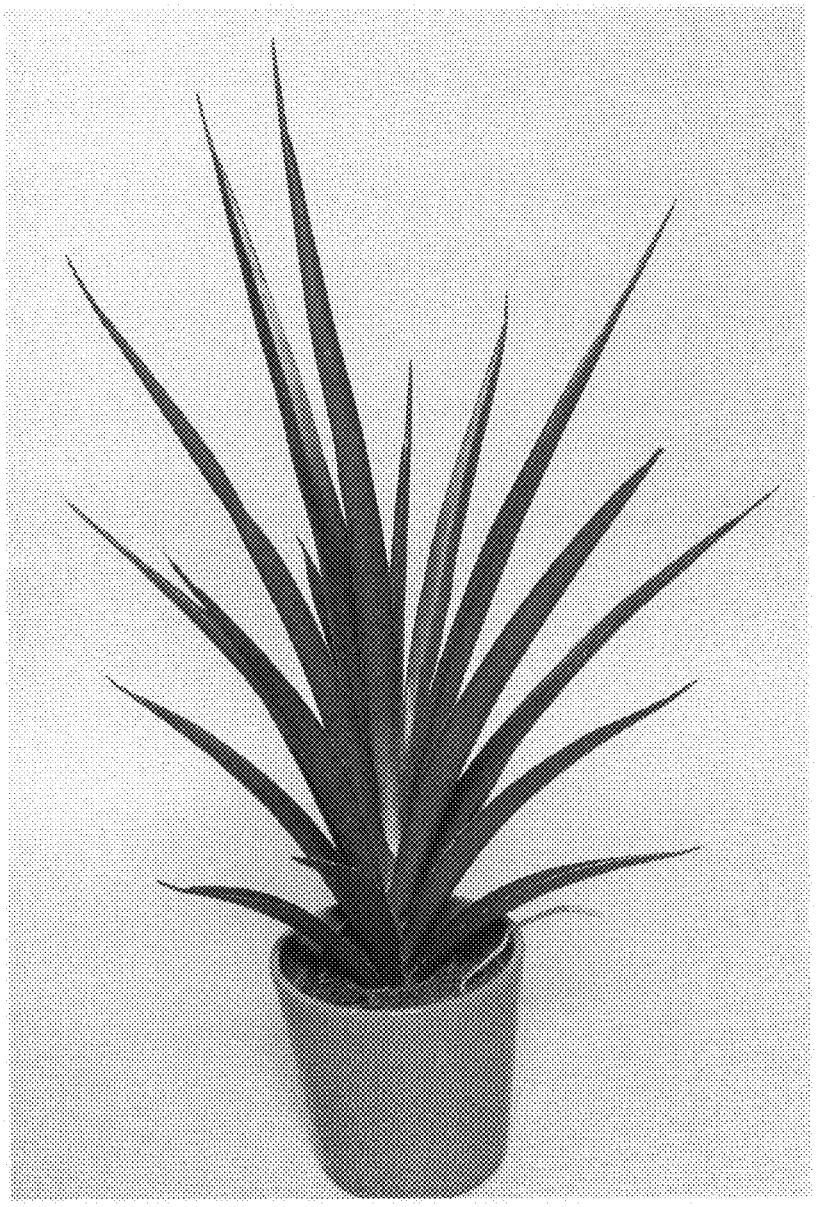

* * * * *